(12) United States Patent
Nakamura et al.

(10) Patent No.: US 7,732,646 B2
(45) Date of Patent: Jun. 8, 2010

(54) CROSSLINKING AGENT BASED ON LINEAR HYDROXYPOLYALLYL ETHER

(75) Inventors: Shin-ichiro Nakamura, Kanagawa (JP); Yasumi Shimizu, Osaka (JP); Tohru Matsutomi, Osaka (JP); Thomas Daniel, Waldsee (DE)

(73) Assignee: Daiso Co., Ltd., Osaka (JP)

( * ) Notice: Subject to any disclaimer, the term of this patent is extended or adjusted under 35 U.S.C. 154(b) by 1173 days.

(21) Appl. No.: 11/025,976

(22) Filed: Jan. 3, 2005

(65) Prior Publication Data
US 2005/0113526 A1 May 26, 2005

Related U.S. Application Data

(62) Division of application No. 10/138,308, filed on May 6, 2002, now abandoned.

(51) Int. Cl.
*C07C 43/04* (2006.01)
*C07C 43/11* (2006.01)

(52) U.S. Cl. .................. 568/680; 568/679; 568/678; 568/673; 568/675; 568/688; 568/689; 252/182.18; 252/182.23; 252/182.24; 252/182.27; 526/317.1; 526/318; 526/320; 526/321

(58) Field of Classification Search .................. 568/680, 568/679, 678, 673, 675, 688, 689; 252/182.18, 252/182.23, 182.24, 182.27; 526/317.1, 526/318, 320, 321
See application file for complete search history.

(56) References Cited

U.S. PATENT DOCUMENTS 6,835,325 B1  12/2004 Nakamura et al.

FOREIGN PATENT DOCUMENTS

| EP | 0 496 067 | 7/1992 |
|---|---|---|
| GB | 1034816 | 7/1966 |
| JP | 3-174414 | 7/1991 |
| JP | 4-236203 | 8/1992 |
| JP | 4-246403 | 9/1992 |
| JP | 10-128108 | 5/1998 |
| JP | 11-140193 | 5/1999 |
| JP | 2001-122922 | 5/2001 |
| WO | 01/29132 | 4/2001 |

OTHER PUBLICATIONS

Smith, P.B., et al. "Allyl Endcapped Polyethylene Oxide Crosslinkers and Their Use in Superabsorbents", J. Polym. Sci. A: Polym. Chem., vol. 35 (1997), pp. 799-806.

*Primary Examiner*—Elvis O Price
(74) *Attorney, Agent, or Firm*—Wenderoth, Lind & Ponack, L.L.P.

(57) ABSTRACT

An allyl type crosslinking agent for use in production of a super water-absorbent polymer comprising a polymerizable compound having a carbon-carbon double bond or a salt thereof. The crosslinking agent comprises a linear hydroxypolyallyl ether having at least one hydroxyl group and at least two allyl groups obtained by allyletherification of hydroxyl groups in a linear polyol compound selected from the group consisting of erythritol, xylitol and sorbitol. This allyl type crosslinking agent is highly soluble in an aqueous solvent, and can give an excellent super water-absorbent polymer, which cannot be obtained in the prior arts, having high levels of both of water absorptivity under atmospheric pressure and water absorptivity under pressurized conditions.

7 Claims, No Drawings

CROSSLINKING AGENT BASED ON LINEAR HYDROXYPOLYALLYL ETHER

This application is a Divisional application of Ser. No. 10/138,308, filed May 6, 2002, now abandoned.

TECHNICAL FIELD

The present invention relates to a crosslinking agent for use in the production of a super water-absorbent polymer crosslinked in an aqueous medium and comprising a polymerizable compound having a carbon-carbon double bond or a salt thereof.

RELATED ART

Most of super water-absorbent polymers comprising polymerizable compounds having polymerizable double bonds (e.g., carbon-carbon double bonds) or salts thereof are based on acrylate salt polymers and produced mainly by polymerization in an aqueous solution. It is proposed to use a wide variety of materials having reactive double bonds, such as acrylate esters, acrylic amides and allyl ethers, as crosslinking agents for crosslinking the super water-absorbent polymers. It is reported that particularly when allyl compounds are used as the crosslinking agent, polymers with particularly excellent water absorptivity can be obtained. Further, the reverse-phase suspension polymerization method polymerizing a monomer and a crosslinking agent dissolved in water suspended in an organic solvent is also industrially carried out, and this reverse-phase suspension polymerization method can also be regarded as the polymerization in an aqueous medium.

For example, it is reported in J. Polym. Sci. A: Polym. Chem. 35, 799 (1977) that polymers obtained by using polyethylene glycol diallyl ether as the crosslinking agent are superior in water absorptivity to the polymers obtained by using an acrylic crosslinking agent. However, the properties of the polyethylene glycol diallyl ether as the crosslinking agent are not satisfactory.

A method of neutralizing polymers obtained by polymerizing acrylic acid is known. JP-A-3-174414, which uses this method, discloses use of tetra-allyloxy ethane as a specific allyl compound. However, this compound suffers from problems such as deficient heat resistance, poor solubility in an aqueous solution of a monomer, and insufficient resistance to hydrolysis. Thus there is demand for development of crosslinking agents having better properties.

Further, JP-A-4-246403 discloses use of triallyl amine, triallyl cyanurate, triallyl isocyanurate and triallyl phosphate. However, these crosslinking agents generally have problems such as deficient heat resistance, adverse effects on polymerization reaction, poor solubility in an aqueous solution of a monomer, and insufficient resistance to hydrolysis, and thus none of these crosslinking agents are practical.

JP-A-11-140193 discloses hydrophilic polymers optionally containing crosslinking monomers. Trimethylol propane tri(meth)acrylate and the like are mentioned as such crosslinking monomers. This prior art document does not describe hydroxypolyallyl ethers derived from erythritol, xylitol and/or sorbitol as the crosslinking monomers.

Generally in the aqueous solution polymerization, an aqueous solution of an acrylic acid monomer is neutralized at a degree of about 75% with e.g., an aqueous solution of sodium hydroxide, then a crosslinking agent is mixed therewith, the monomer is polymerized by a polymerization initiator, and the formed solid is cut into pieces of suitable size and then dried (hereinafter, this method is referred to as "post-neutralization polymerization method"). However, if the crosslinking agent is sparingly soluble in the aqueous solution after neutralization, the crosslinking agent is dissolved in an aqueous solution of acrylic acid, and the solid formed by polymerization is cut and neutralized (hereinafter, this method is referred to as "pre-neutralization polymerization method"). This method as compared with neutralization in solution form is disadvantageous in production efficiency and uneven neutralization of the product.

SUMMARY OF THE INVENTION

The object of the present invention is to provide a novel allyl type crosslinking agent soluble in an aqueous solution of a monomer (e.g., an aqueous solution of an acrylate salt) and free of the problems possessed by the prior art, in order to produce a super water-absorbent polymer having particularly excellent water-absorptivity among water-absorptivity required at practical levels.

The present inventors found that, as the allyl compound for solving the problems described above, a linear hydroxypolyallyl ether having at least two allyl ether groups derived from a linear polyol compound is industrially useful not only in the above-mentioned pre-neutralization polymerization method but also in the above-mentioned post-neutralization polymerization method, and thus completed the present invention.

The present invention provides a crosslinking agent for use in the production of a super water-absorbent polymer comprising a polymerizable compound having a carbon-carbon double bond or a salt thereof, comprising a linear hydroxypolyallyl ether having at least one hydroxyl group and at least two allyl groups obtained by allyletherification of hydroxyl group in a linear polyol compound which has a straight-chain carbon skeleton, which has carbon atoms each having one hydroxyl group, and which is represented by the formula (1):

$$HOCH_2[CH(OH)]_nCH_2OH \qquad (1)$$

wherein n is an integer of from 2 to 8.

DETAILED EXPLANATION OF THE INVENTION

When the linear hydroxypolyallyl ether according to the present invention is used as the crosslinking agent for high water-absorbance, it imparts an effective water absorptivity, and it provides a super water absorptivity crosslinking agent having remarkably improved properties, particularly in the view point of a high level of water absorbance under both of a normal pressure and an increased pressure and in the view point of a low concentration of the crosslinking agent at which said high level of water absorbance is achieved, in comparison with other polyallyl derivative crosslinking agents used in the conventional technology or polyacryl derivative crosslinking agents. As the crosslinking agent for the super water absorbent polymer, for example, a "polyallyl ether" compound is generally described in JP-A-10-128108, and a compound having close relation to the crosslinking agent of the present invention is generally described as in JP-A-11-140193 and JP-A-4-236203. However, significant effects of the crosslinking agent of the present invention cannot be expected from extension of the prior arts.

In the present invention, the linear hydroxypolyallyl ether is used as a crosslinking agent for the production of super water-absorbent polymers. The crosslinking agent comprises one linear hydroxypolyallyl ether or a mixture of at least two linear hydroxypolyallyl ethers. The molecule of the linear hydroxypolyallyl ether has at least one hydroxyl group and at least two allyl groups. The number of hydroxyl groups is at least one, for example at least two, and specific example of the number of hydroxyl groups is from 1 to 8, particularly from 1 to 4. The number of allyl groups is at least 2, for example at least 3, specifically from 2 to 8, particularly from 3 to 5. In the case of the mixture of linear hydroxypolyallyl ethers, an average number of hydroxyl groups is at least 0.5, for example at least 1.0, particularly at least 1.5, and an average number of allyl groups is at least 2.0, for example at least 2.5, particularly at least 3.0. The numbers of hydroxyl groups and allyl groups (including the average numbers thereof) are determined by NMR (particularly, $^1$H NMR). At least one allyl group may be present in a linear hydroxypolyallyl ether molecular chain excluding molecular chain terminals.

The linear hydroxypolyallyl ether can be obtained generally by allyletherification of at least two hydroxyl groups among the hydroxyl groups in a linear polyol compound. Allyletherification can be conducted by using an allyl etherifying agent. In the allyletherification of the linear polyol compound, a hydrogen atom in the hydroxyl groups is replaced by an allyl group.

The linear polyol compound is a compound having a straight-chain carbon skeleton, having carbon atoms each having one hydroxyl group, and represented by the formula (1):

$$\mathrm{HOCH_2[CH(OH)]}_n\mathrm{CH_2OH} \qquad (1)$$

wherein n is an integer of from 2 to 8. In particular, n may be from 2 to 4, and the linear polyol compound may be erythritol, xylitol and/or sorbitol.

The allyl etherifying agent is a compound having an allyl group and a reactive group. The allyl group may be bound to the reactive group by means of a direct bond, but may also be bound by means of a divalent organic group (e.g., substituted or unsubstituted hydrocarbon group (e.g., $C_1$ to $C_{10}$)). Usually, the allyl etherifying agent comprises one allyl group and one reactive group which are bonded by means of a direct bond.

Examples of the reactive group in the allyletherifying agent include a halogen atom, an alkyl sulfonyloxy group (number of carbon atoms in the alkyl group is e.g., from 1 to 10), an aryl sulfonyloxy group (number of carbon atoms in the aryl group is e.g., from 6 to 20), and an aralkyl sulfonyloxy group (number of carbon atoms in the aralkyl group is e.g., from 7 to 30).

Examples of the halogen atom include chlorine and bromine.

Examples of the alkyl sulfonyloxy group include a methyl sulfonyloxy group, an ethyl sulfonyloxy group, a n-propyl sulfonyloxy group, an isopropyl sulfonyloxy group, a n-butyl sulfonyloxy group, a n-octyl sulfonyloxy group, a trifluoromethane sulfonyloxy group, a trichloromethane sulfonyloxy group, a 2-chloro-1-ethane sulfonyloxy group, a 2,2,2-trifluoroethane sulfonyloxy group, a 3-chloropropane sulfonyloxy group, and a perfluoro-1-butane sulfonyloxy group.

Examples of the aryl sulfonyloxy group include a benzene sulfonyloxy group, a 2-aminobenzene sulfonyloxy group, a 2-nitrobenzene sulfonyloxy group, a 2-methoxycarbonyl benzene sulfonyloxy group, a 3-aminobenzene sulfonyloxy group, a 3-nitrobenzene sulfonyloxy group, a 3-methoxycarbonyl benzene sulfonyloxy group, a p-toluene sulfonyloxy group, a 4-tert-butyl benzene sulfonyloxy group, a 4-fluorobenzene sulfonyloxy group, a 4-chlorobenzene sulfonyloxy group, a 4-bromobenzene sulfonyloxy group, a 4-iodobenzene sulfonyloxy group, a 4-methoxybenzene sulfonyloxy group, a 4-aminobenzene sulfonyloxy group, a 4-nitrobenzene sulfonyloxy group, a 2,5-dichlorobenzene sulfonyloxy group, a pentafluorobenzene sulfonyloxy group, a 1-naphthalene sulfonyloxy group, and a 2-naphthalene sulfonyloxy group.

Examples of the aralkyl sulfonyloxy group include an α-toluene sulfonyloxy group, a trans-β-styrene sulfonyloxy group, and a 2-nitro-α-toluene sulfonyloxy group.

Examples of the allyletherifying agent include an allyl halide, an alkyl sulfonyloxyallyl, an aryl sulfonyloxyallyl, and an aralkyl sulfonyloxyallyl.

Examples of the allyl halide include allyl chloride and allyl bromide.

Examples of the alkyl sulfonyloxyallyl include methyl sulfonyloxyallyl, ethyl sulfonyloxyallyl, n-propyl sulfonyloxyallyl, isopropyl sulfonyloxyallyl, n-butyl sulfonyloxyallyl, n-octyl sulfonyloxyallyl, trifluoromethane sulfonyloxyallyl, trichloromethane sulfonyloxyallyl, 2-chloro-1-ethane sulfonyloxyallyl, 2,2,2-trifluoroethane sulfonyloxyallyl, 3-chloropropane sulfonyloxyallyl, and perfluoro-1-butane sulfonyloxyallyl.

Examples of the aryl sulfonyloxyallyl include benzene sulfonyloxyallyl, 2-aminobenzene sulfonyloxyallyl, 2-nitrobenzene sulfonyloxyallyl, 2-methoxycarbonyl benzene sulfonyloxyallyl, 3-aminobenzene sulfonyloxyallyl, 3-nitrobenzene sulfonyloxyallyl, 3-methoxycarbonylbenzene sulfonyloxyallyl, p-toluene sulfonyloxyallyl, 4-tert-butyl benzene sulfonyloxyallyl, 4-fluorobenzene sulfonyloxyallyl, 4-chlorobenzene sulfonyloxyallyl, 4-bromobenzene sulfonyloxyallyl, 4-iodobenzene sulfonyloxyallyl, 4-methoxybenzene sulfonyloxyallyl, 4-aminobenzene sulfonyloxyallyl, 4-nitrobenzene sulfonyloxyallyl, 2,5-dichlorobenzene sulfonyloxyallyl, pentafluorobenzene sulfonyloxyallyl, 1-naphthalene sulfonyloxyallyl, and 2-naphthalene sulfonyloxyallyl.

Examples of the aralkyl sulfonyloxyallyl include α-toluene sulfonyloxyallyl, trans-β-styrene sulfonyloxyallyl and 2-nitro-α-toluene sulfonyloxyallyl.

The following method is generally used to prepare the linear hydroxypolyallyl ether by allyletherification of the linear polyol compound.

One part by mol of the linear polyol compound, y part by mol of potassium hydroxide or sodium hydroxide, and 10 to 50 wt-% of water or an aprotic polar solvent (e.g., acetonitrile, tetrahydrofuran, dioxane, and dimethyl formaldehyde) are introduced into a suitable reaction vessel equipped with a stirrer, a thermometer and a reflux condenser. The mixture is heated at about 50° C. to 150° C. under stirring, then y part by mol of the allyletherifying agent is added dropwise, and the mixture is reacted for about 2 hours to 40 hours. The amount of the alkali (e.g., an alkali metal hydroxide such as sodium hydroxide) and the allyletherifying agent may be considerably higher than y part by mol. If necessary, an alcohol or a catalyst such as quaternary ammonium salt may be present in the reaction system. After the completion of the reaction, the resultant liquid layer is separated from the precipitated solid and purified by conventional techniques such as distillation, extraction, recrystallization and liquid chromatography. Sodium hydroxide or potassium hydroxide may be added dropwise as an aqueous solution to the reaction system, simultaneously with adding the allyletherifying agent.

In a preferable embodiment of the present invention, the linear hydroxypolyallyl ether is a compound obtained by allyletherification of at least three hydroxyl groups in the linear polyol compound.

Examples of such linear hydroxypolyallyl ether include erythritol triallyl ether, xylitol triallyl ether, xylitol tetraallyl ether, sorbitol triallyl ether, sorbitol tetraallyl ether, and sorbitol pentaallyl ether.

In the present invention, a linear hydroxypolyallyl ether having two allyl groups may be used. Examples of such linear hydroxypolyallyl ethers include erythritol diallyl ether, xylitol diallyl ether, and sorbitol diallyl ether.

Sorbitol polyallyl ether is preferable, in view of easy available raw materials, and in view of a wide application range of concentration due to high solubility of the crosslinking agent. Sorbitol triallyl ether and sorbitol tetraallyl ether are particularly preferable.

In production of a super water-absorbent polymer, the crosslinking agent of the present invention is used for the purpose of crosslinking said polymer. Generally, a super water-absorbent polymer is crosslinked in an aqueous medium with the crosslinking agent of the present invention.

Generally, the crosslinking agent of the present invention is used in the production of a super water-absorbent polymer polymerized in an aqueous medium and comprising a polymerizable compound having a carbon-carbon double bond or a salt thereof. In production of the super water-absorbent polymer, said polymerizable compound and/or a salt thereof can be used as the monomer.

A repeating unit in the super water-absorbent polymer has a functional group. Examples of the functional group include a carboxyl group, a hydroxyl group, an amide group and an acetamide group.

Examples of the super water-absorbent polymer include an acrylic acid-based polymer, a vinyl alcohol-based polymer, an isobutylene/maleic anhydride-based polymer, an acrylamide-based polymer, an acrylamide/acrylic acid-based polymer, and an N-vinyl acetamide-based polymer. Generally, a monomer forming the super water-absorbent polymer has the functional group. In production of a certain polymer such as polyvinyl alcohol, however, a vinyl ester such as vinyl acetate or vinyl propionate may be used as the monomer, and then a functional group such as a hydroxyl group may be introduced into the synthesized polymer.

Examples of the monomer forming the super water-absorbent polymer include acrylic acid, methacrylic acid, maleic acid, fumaric acid, itaconic acid, crotonic acid, citraconic acid, α-hydroxyacrylic acid, aconitic acid, 2-(meth)acryloylethane sulfonic acid, 2-(meth)acrylamide-2-methylpropane sulfonic acid and salts thereof. Examples of the salts include metal salts. Examples of metals in the salts are alkali metals (e.g., potassium and sodium).

The crosslinking agent is preferably dissolved in a mixture of the monomer and an aqueous medium. The solubility of the crosslinking agent in 100 mL of the mixture of the monomer and the aqueous medium is at least 0.2 g, for example at least 0.4 g, particularly at least 1 g, especially at least 5 g. The aqueous medium consists of water only or comprises water and a water-soluble organic solvent (e.g., alcohol).

The super water-absorbent polymer may be based on a complete or partial salt of carboxylic acid.

The crosslinking agent of the present invention can be used in any methods known in the art, which are not limited. For example, 60 to 90 mol-% of an aqueous solution of an acrylic acid monomer is neutralized with e.g., an aqueous solution of sodium hydroxide to form 30 to 50 weight-% aqueous solution, then the crosslinking agent is mixed in an amount of 0.1 to 1.0 weight-%, a redox radical polymerization initiator such as an azo compound or a peroxide is added thereto, the monomer is polymerized usually at a temperature of at most about 100° C., and the formed polymer is cut into pieces of suitable size and then dried, whereby the super water-absorbent polymer can be produced (a post-neutralization polymerization method).

Alternatively, the crosslinking agent and the polymerization initiator are added to an aqueous solution of an acrylic acid monomer not neutralized, then the monomer is polymerized, and the formed solid is cut into pieces of suitable size and neutralized with sodium hydroxide (a pre-neutralization polymerization method).

The crosslinking agent of the present invention may consist of the hydroxypolyallyl ether only or a liquid mixture such as an aqueous solution of the hydroxypolyallyl ether.

The super water-absorbent polymer polymerized in the presence of the crosslinking agent of the present invention may be in the form of a water-absorbent polymer having higher properties prepared by a method in which surfaces of the polymeric particles are treated with a specified agent (for example, a surface treatment agent) for the purpose of decreasing a blocking property among polymeric particles prepared by comminution according to conventional procedures such as U.S. Pat. No. 5,597,873 and JP-A-5-138019.

The surface treatment agent is referred to also as a "surface crosslinking agent". Examples of the surface treatment agent include a dihydric alcohol such as ethylene glycol, propylene glycol, butane diol, diethylene glycol, triethylene glycol and polyethylene glycol; a polyhydric alcohol (an alcohol having valence of at least three) such as glycerine, polyglycerine, trimethylolpropane, pentaerythritol, sorbitol and polyvinyl alcohol; an amine compound such as diethanolamine, triethanolamine, N-(hydroxyalkyl)-(meth)alanine ester, a polyamine/epichlorohydrin adduct and a polyethylene/polyamine/epichlorohydrin adduct; a polyglycidyl compound such as ethyleneglycol diglycidyl ether; a carbonate compound such as ethylene carbonate. The amount of the surface treatment agent may be from 0.01 to 20 parts by weight, preferably from 0.1 to 10 parts by weight, particularly preferably from 0.1 to 5 parts by weight, based on 100 parts by weight of the dried polymer obtained by the polymerization reaction. The polymer contacted with the treatment agent may be thermally treated by the use or non-use of an organic solvent or an aqueous solvent. The heat temperature may be from 50 to 300° C., preferably from 80 to 250° C., more preferably from 100 to 200° C.

PREFERRED EMBODIMENTS OF THE INVENTION

Hereinafter, the present invention is illustrated with reference to the

EXAMPLES AND COMPARATIVE EXAMPLES

The water absorptivity of a powdery polymer (amount of absorbed water (g) per 1 g of the powdery polymer) was evaluated in the following manner.

About 0.2 g powdery polymer is accurately weighed, introduced uniformly into a tea bag-type bag made of non-woven fabric (6.8 mm×9.6 mm), and immersed in a 0.9% saline solution, and the weight thereof after immersed for 1 hour is measured. The procedure is conducted under atmospheric pressure (1 atm). Taking that the weight of the bag only is the blank, the water absorptivity of the powdery polymer is calculated according to the following equation:

Water absorptivity=[(weight (g) after water absorption)−(blank (g))]/[weight (g) of super water-absorbent polymer]

(1) Production of Crosslinking Agent

Example 1

455 g (2.5 mol) of D-sorbitol, 421 g (7.5 mol) of potassium hydroxide and 150 mL of water were introduced into a 2 L four-necked flask equipped with an agitator, a dropping funnel, a reflex condenser, a thermometer and a mechanical stirrer, and the mixture was stirred under heating on a mantle heater to give a slightly turbid pale yellow solution having a temperature of 135° C. Upon the initiation of dropwise addition of allyl bromide thereto, the refluxing was initiated and the liquid temperature was lowered to about 95° C. Thereafter, gentle refluxing was continued while the liquid temperature was kept at about 90 to 105° C. during dropwise addition. 910 g of allyl bromide (7.5 mol) was added dropwise over the period of 6 hours, and the temperature of the solution was 86° C. after this addition. Thereafter, the mixture was further heated under reflux for 4 hours and then gradually cooled, and this reaction mixture was removed. This mixture had been separated into an organic layer, a small amount of an aqueous layer and a large amount of crystalline solids. This organic layer (468 g) was taken while the crystalline solids and the aqueous layer were washed with diethyl ether, and the washing liquids were combined with the organic layer. This mixture was concentrated in an evaporator at 40° C. to give 434 g of a concentrated liquid. The resultant oily liquid was analyzed by a liquid chromatography (analytical conditions were as follows: column: ODS-120-5-AP manufactured by Daiso Co., Ltd., column temperature: 25° C., eluent: methanol/water (4:1) at a flow rate of 1 ml/min.). The analysis results are shown in Table 1, indicating that a mixture of D-sorbitol allyl ethers was obtained. The average degree of allylation (that is, the average number of allyl groups) per one molecule was about 3.0 as determined by $^1$H NMR.

TABLE 1

| Compound | Number of allyl groups per molecule | Ratio of area (%) by liquid chromatography |
| --- | --- | --- |
| D-sorbitol monoallyl ether | 1 | 2.15 |
| D-sorbitol diallyl ether | 2 | 17.14 |
| D-sorbitol triallyl ether | 3 | 43.16 |
| D-sorbitol tetraallyl ether | 4 | 22.51 |
| D-sorbitol pentaallyl ether | 5 | 13.40 |
| D-sorbitol hexaallyl ether | 6 | 1.01 |

The solubility of this mixture in an aqueous acrylate salt solution was determined in the following manner.

180 g of acrylic acid, 75 g of sodium hydroxide, and 424 g of distilled water were mixed to prepare a standard aqueous solution of acrylate salt having a monomer concentration of 32.4 wt-% and a degree of neutralization of 75 mol-%.

10 g of the mixture obtained in the above experiment was added to 100 g of the standard aqueous solution of acrylate salt, then shaken vigorously and left to be separated into 2 layers, and an aqueous layer was removed and analyzed by a liquid chromatography (analytical conditions were as follows: column: ODS-120-5-AP manufactured by Daiso Co., Ltd., column temperature: 25° C., eluent: methanol/water (4:1) at a flow rate of 1 ml/min.), indicating that the solubility was 1.34 w/v %.

Comparative Example 1

10 g of trimethylol propane triacrylate was mixed with 100 g of the above-mentioned standard aqueous solution of acrylate salt, then shaken vigorously and left to be separated into 2 layers, and an aqueous layer was removed and analyzed by a gas chromatography (analytical conditions were as follows: column: 30 m, BP20-0.25 manufactured by SGE Co., Ltd., column temperature: from 100 to 200° C. at an increasing temperature of 10° C./min.), indicating that the solubility was 0.20 w/v %.

The solubility in the standard aqueous solution of acrylate salt in Example 1 and Comparative Example 1 is summarized in Table 2.

TABLE 2

| Compound | Example 1 | Comparative Example 1 |
| --- | --- | --- |
|  | Mixture of D-sorbitol allyl ethers | Trimethylol propane triacrylate |
| Average degree of allylation | 3.0 | — |
| Solubility (w/v %) in standard aqueous solution of acrylate salt | 1.34 | 0.20 |

The compound in Example 1 was superior in the solubility in the standard aqueous solution of acrylate salt to the compound in Comparative Example 1.

(2) Production of a Water-absorbent Polymer

Example 2

180 g (2.5 mol) of acrylic acid, 75 g (1.875 mol) of NaOH, 424 mL of water and 1.44 g (4.78 mmol) of the D-sorbitol allyl ether mixture obtained in Example 1 were introduced into a 1 L separable flask equipped with a nitrogen inlet (for use in liquid and gaseous phase), a thermometer, a dropping funnel and a mechanical stirrer, and the mixture was cooled to a temperature of 5° C. on ice. The mixture at this stage was a colorless transparent liquid having a pH value of 5 to 6. The separable flask was placed in a thermal insulating container, and then a solution of 150 mg (0.56 mmol) 2,2'-azobis(2-amidinopropane)dihydrochloride in 1 mL water, a solution of 20 mg (0.113 mmol) L-ascorbic acid in 1 mL water and a solution of 100 mg (0.91 mmol) of 31% aqueous hydrogen peroxide in 1 mL water were added thereto successively within 1 minute. Just after these materials were added, the turbidity of the mixture was increased, and the viscosity was increased in an exothermic reaction to terminate stirring. The reaction mixture was left to stand and it reached the maximum temperature (82° C.) after 19 minutes. Thereafter, the reaction mixture was left and gradually cooled to room temperature, and the resultant colorless transparent gel was removed from the flask. Apart (about 100 g) of this gel was removed and comminuted by a speed cutter. When the size of the resultant particles was reduced to about 1 mm or less, the particles were dried for 5 hours in an oven at 180° C. The resultant solids were removed from the oven to give 28.0 g of pale yellow solids. These were ground into powder in a sample mill, placed again in the oven (180° C.), and dried for 1.5 hours. After 25.9 g of pale yellow powder was thus obtained, the powder was sieved to give 22.1 g of powder having a particle diameter of at least 60 μm.

The powdery polymer thus prepared was evaluated for water absorptivity. The water absorptivity under atmospheric pressure was 46 g/g.

Comparative Example 2

A powdery polymer was prepared in the same manner as in Example 2 except that 1.41 g (4.78 mmol) of trimethyl propane triacrylate was used in place of 1.44 g (4.78 mmol) of the D-sorbitol allyl ether mixture. The water absorptivity under atmospheric pressure was 36 g/g.

Example 3

180 g (2.5 mol) of acrylic acid, 487 mL of water and 1.44 g (4.78 mmol) of the D-sorbitol allyl ether mixture obtained in Example 1 were introduced into a 1 L separable flask equipped with a nitrogen inlet (for use in liquid and gaseous phase), a thermometer, a dropping funnel and a mechanical stirrer, and the mixture was cooled to a temperature of 5° C. on ice. The mixture at this stage was a colorless transparent liquid. The separable flask was placed in a thermal insulating container, and then a solution of 150 mg (0.56 mmol) 2,2'-azobis(2-amidinopropane) dihydrochloride in 1 mL water, a solution of 20 mg (0.113 mmol) L-ascorbic acid in 1 mL water and a solution of 100 mg (0.91 mmol) of 31% aqueous hydrogen peroxide in 1 mL water were added thereto successively within 1 minute. Just after these materials were added, the turbidity of the mixture was increased, and the viscosity was increased in an exothermic reaction to terminate stirring. The reaction mixture was left to stand and it reached the maximum temperature (83° C.) after 20 minutes. Thereafter, the reaction mixture was left and gradually cooled to room temperature, and the resultant colorless transparent gel was removed from the flask. A part (about 100 g) of this gel was removed and divided by a speed cutter. When the size of the resultant particles was reduced to about 1 mm or less, 23.5 g of 48% aqueous sodium hydroxide was added thereto, and the particles were further divided for 30 minutes. The resultant divided gel mixture was dried for 5 hours in an oven at 180° C. to give 28.56 g of pale yellow solids. These were ground into powder in a sample mill, placed again in the oven (180° C.), and dried for 1.5 hours. After 26.2 g pale yellow powder was thus obtained, the powder was sieved to give 23.2 g powder having a particle diameter of at least 60 μm.

The powdery polymer thus prepared was evaluated for water absorptivity, indicating that the water absorptivity was 46 g/g under atmospheric pressure.

(I) Preparation and Solubility of Crosslinking Agent

Example 4

Sorbitol Allyl Ether Mixture 859 g of a 70% aqueous D-sorbitol solution, 583 g of a 48% aqueous sodium hydroxide solution and 60 mL of allyl alcohol were charged into a 2,000 mL reactor equipped with an agitator, a reflex condenser, a thermometer and two dropping funnels, and the mixture was heated. When the mixture reached 90° C., the dropwise addition of allyl chloride from one of the dropping funnels was initiated. The dropwise addition amount was adjusted so as to maintain the temperature to at least 70° C., while whole of a reflux liquid is returned to the reactor.

At 3.7 hours after the initiation of the reaction, the addition of 200 g of allyl chloride was completed. Then the addition was continued. The time required for adding 300 g of allyl chloride was 5.5 hours after the initiation of the reaction. At this point of time (at the time at which allyl halide was added in the amount of 20% by mol, based on total molar number of hydroxyl group contained in D-sorbitol), the reflux liquid is separated so that an oil layer alone is returned to the reactor by attaching a water metering reservoir between the reflux condenser and the reactor. The time required for adding total amount of 459 g of allyl chloride was 8 hours after the initiation of the reaction. At this point of time, the dropwise addition of 333 g of 48% aqueous sodium hydroxide solution from the other dropping funnel was initiated. The time required for adding total amount of 842 g of allyl chloride was 11 hours after the initiation of the reaction. The temperature was between 70° C. and 90° C. After the mixture was digested for one hour, the mixture was cooled.

A reaction product was a mixture slurry of a yellowish brown oil and a solid particles and did not have an aqueous layer. The oil, remaining after low-boiling point substances are distilled off, was analyzed according to a gas chromatography and $^1$H NMR. The composition (% by weight) was as follows. D-sorbitol: 0.0%, D-sorbitol monoallyl ether: 0.4%, diallyl ether: 11.3%, triallyl ether: 35.4%, tetraallyl ether: 40.5%, pentaallyl ether: 12.9%, hexaallyl ether: 0.2%. An average molar number of allyl groups added to one molecule of D-sorbitol was 3.5.

The crosslinking agent prepared according to the present method is referred to as "crosslinking agent (A)".

A given amount of the crosslinking agent (A) was weighed in a screw tube, and water was added to give mixtures having a concentration of 3.0%, 2.0%, 1.0% and 0.9%. The tube containing each mixture was vigorously shaken and stood in a temperature-controlled bath at 20° C. The tube was removed after 30 minutes, the tube was vigorously shaken for at most 30 seconds which was such time that the liquid temperature was kept, and then the tube was stood again in the temperature-controlled bath. After one hour, the tube was removed from the temperature-controlled bath and then the liquid state was quickly visually observed. Since the opaqueness was observed at the concentrations of 3.0% and 2.0%, and the layer separation or opaqueness is not observed at the concentrations of 1.0% and 0.9%, the solubility of the crosslinking agent (A) according to the present invention was determined to be from 1% to 2%.

Comparative Example 3

Preparation and Solubility Measurement of Pentaerythritol Allyl Ether Mixture 272 g (2.0 mol) of pentaerythritol, 337 g (6.0 mol) of potassium hydroxide and 150 mL of water were charged into a 2 L four-necked flask equipped with an agitator, a dropping funnel, a reflex condenser, a thermometer and mechanical stirrer, and the mixture was heated on a mantle heater with stirring to give a solution having 120° C. The initiation of the dropwise addition of allyl bromide gave the initiation of reflux to decrease the temperature to about 95° C. During the dropwise addition, the mild reflux was continued while the liquid temperature was from about 90° C. to about 105° C. Totally 726 g (6.0 mol) of allyl bromide was dropwise added for 8 hours. After the completion of dropwise addition of allyl bromide, the liquid temperature was 93° C. After the completion of dropwise addition of allyl bromide, the liquid was heated for 4 hours with stirring. Then the liquid was kept stand without heating and the reaction mixture was removed. The reaction mixture had separated phases of an organic phase, an aqueous phase and a large amount of crystalline solid. The organic phase was removed. This mixture was concentrated in an evaporator at 40° C. to give 458 g of an oil. A gas chromatography analysis [analysis conditions are as follows: Column: BP20-0.25 (trade name, manufactured by SGE Corp.), column temperature: 100° C. to 200° C., temperature increase rate: 10° C./min.] of the resultant oil gave results (area ratio) as follows. A pentaerythritol allyl ether mixture was obtained. An average allylation amount per one molecule according to $^1$H NMR was about 3.0.

TABLE I

| Compound | Value of y (number of ally groups per one molecule) | Area ratio according to gas chromatography (%) |
| --- | --- | --- |
| Pentaerythritol diallyl ether | 2 | 11.4 |
| Pentaerythritol triallyl ether | 3 | 80.7 |
| Pentaerythritol tetraallyl ether | 4 | 7.4 |

The solubility of this mixture in an aqueous acrylate salt solution was determined as follows. 10 g of the mixture obtained in the above experiment was added to 100 g of the above-mentioned standard aqueous solution of acrylate salt, then shaken vigorously and left to be separated into 2 layers, and an aqueous layer was removed and analyzed by a gas chromatography [analysis conditions are as follows: Column: BP20-0.25 (trade name, manufactured by SGE Corp.), column temperature: 100° C. to 200° C., temperature increase rate: 10° C./min.]. The solubility was 0.40 w/v %.

Reference Example 1

Crosslinking Agent (a) (P-30, Pentaerythritol Triallyl Ether)

10.0 mg, 21.4 mg or 61.8 mg of P-30 (pentaerythritol triallyl ether manufactured by Daiso Co., Ltd.) was weighed into each of three 30 mL screw tubes and 20.0 g of water was added to each tube to give mixtures each having a concentration of 0.05%, 0.11% or 0.31%. The mixtures were treated in a temperature-controlled bath at 20° C. as in Example 4.

No opaqueness was observed in the concentration of 0.05%, slight opaqueness was observed in the concentration of 0.11%, and opaqueness was observed in the concentration of 0.31%. The solubility of the crosslinking agent P-30 in water was determined as "from 0.05% to 0.11%".

Reference Example 2

Synthesis of Crosslinking Agent (b): Ethyleneglycol Diallyl Ether

Into 500 mL three-necked flask equipped with a dropping funnel, a thermometer, a reflux condenser and magnetic stirrer, 180 g of acetonitrile, 48.0 g (1,200 mmol) of NaOH pellets and 12.4 g (200 mmol) of ethyleneglycol were charged with stirring to give an opaque mixture having a temperature of 60° C. 96.8 g (800 mmol) of allyl bromide was further dropwise added, and the stirring was continued for 4 hours. After left and gradually cooled to room temperature, the mixture was filtered and the filtered solid was washed with a small amount of ether. A filtrate and a washing liquid were combined. The resultant solution was distilled at atmospheric pressure. After a large amount of acetonitrile was filtered off at the beginning of distillation, 22 g of a distillation fraction having a boiling temperature of 132 to 140° C. was obtained. This distillation fraction contained 78%, 6% of monoallyl product according to a gas chromatography. This fraction was distilled again to give the objected product (b).

(II) Preparation of Water-absorbent Polymer

Hereinafter, the water absorptivity of the super water-absorbent polymer was evaluated as follows:

a) Measurement of Water Absorption Amount at Atmospheric Pressure (AC: Absorbency Capacity)

About 0.2 g of Highly water-absorbent resin particles are precisely weighed (Ws (g)). The resin particles are uniformly charged into a tea bag-type bag (size: 6.8 mm×9.6 mm for enclosure part) made of non-woven fabric. The bag is immersed into a 0.9% saline solution. After one hour immersion, the bag is removed from the solution. The bag is placed on a paper board and left for one minute so that the paper board roughly absorbs water. The bag is transferred and placed on another new paper board and left for 30 minutes. Then the weight (W1 (g)) of the bag is measured. W0 (g) is a blank weight wherein a bag containing no resin sample is immersed into a 0.9% saline solution. The above procedure was conducted using two bags containing the same resin and two blank bags containing no resin. An average of two numerical values is taken as a measurement value. The experiment is conducted at room temperature (about 20° C.).

A previous experiment reveals that good repetition can be obtained since a weight decrease is most stable at the time of 20 minutes to 40 minutes in the conditions left on the board paper.

The AC value is calculated by the following equation:

$$AC(g/g)=(W1-W0)/Ws$$

b) Measurement of Water Retention Amount in Centrifugally Treated Water-absorbed Polymer (CRC: Centrifuge Retention Capacity)

About 0.5 g of a gel having absorbed water in the above AC measurement test is charged into a 1.5 mL sample vessel having a inner diameter of 7 mm which has a mesh screen at a bottom so as to filter off the dehydrated water. The weight of the gel contained in the vessel is precisely measured. The gel is dehydrated with a high speed micro-centrifuge separator (MTX-160, TOMY) for 20 minutes at 10° C. and 15,000 rpm. The weight of the gel after the dehydration treatment is measured so that a weight decrease ratio D (% by weight) to the weight before the dehydration treatment is determined. The CRC is calculated according to the following equation:

$$CRC(g/g)=AC(g/g)\times(100-D)/100$$

c) Measurement of Water Absorption Amount Under Pressurized Conditions (AUP: Absorbency Under Pressure)

About 0.2 g of SAP particles are charged into an acryl tube having an inner diameter of 30.7 mm and a length of 100 mm wherein one end of the tube is capped with a metal mesh having 325 mesh. The SAP particles (Ws(g)) contained in the tube are precisely weighed and are almost uniformly spread. An acryl rod (inner tube) having an outer diameter of 30 mm is inserted into the above-mentioned acryl tube so that the inner tube reaches the bottom end. Then the weight (W1) is measured. Lead weights are positioned on the inner tube so that the total weight of the inner tube and the lead weights is 346 g. 3 sets of this measurement instrument and one set of blank instrument containing no sample are provided. Four sets are positioned on a vat, and a 0.9% saline solution is poured into the vat so that the mesh is sufficiently immersed in the saline solution. After left for one hour, the lead weights are took away and water drops attached to the tube are wiped off and the weight of tubes is measured. A weight difference between the sets after and before immersion, that is, gel weight (W1)(g) is determined. An average weight of gel (W1 (g)) in three sets is taken as the measurement value for the sample set. In the same manner, the weight difference for the blank is measured and taken as W0 (g).

The AUP is calculated according to the following equation:

$$AUP(g/g)=(W1-W0)/Ws$$

Examples 5 to 10

(II)-1 Polymerization Reaction (Pre-neutralization Polymerization Method);

Examples 5 to 7

Synthesis of Super Water-absorbent Polymer 180 g (2.5 mol) of acrylic acid and 487 g of water are charged into a 1 L separable flask equipped with a nitrogen introducing tube, a thermometer, a dropping funnel and a stirrer, and stirred and cooled with ice under nitrogen atmosphere to have a temperature of about 10° C. The crosslinking agent (A) was added in a concentration shown in Table 3 and nitrogen was bubbled for 30 minutes in the mixture while stirred and cooled with ice to give a mixture temperature of about 5° C.

After the reaction flask was placed into a vessel filled with a thermally insulating material, a solution of 200 mg (0.74 mmol) of 2,2'-azobis(2-amidinopropane) dihydrochloride in 1 mL of water, a solution of 33.4 mg (0.19 mmol) of L-ascorbic acid in 1 mL of water, and a solution of 108 mg (0.98 mmol) of 31% aqueous hydrogen peroxide in 1 mL water were added. The mixture increasingly had higher viscosity with evolving heat. At the time of stirring the mixture with difficulty, the stirring is discontinued. The mixture became a gel, which was allowed to stand. The reaction temperature reached a maximum temperature of 65° C. to 75° C. after about 10 to 20 minutes, depending on the conditions. The mixture was allowed to stand so as to be gradually cooled and was kept to stand for one night.

About 100 g of the resultant gel was placed into a rotary cutter, and comminuted to have particle size of about 1 mm. The rotary comminution was conducted by adding a solution in 20 mL water of NaOH (11.2 g) corresponding to 75% based on equivalent of free carboxylic acid contained in the gel calculated from charged acrylic acid amount.

The resultant comminuted gel was dried at 140° C. for 6 hours in an air flow oven with confirming a constant weight to give a dry solid. The resultant dry solid was treated with a sample mill, and sieved. The particles having the particle size of at least about 63 μm were taken as a super water-absorbent polymer without surface crosslinking treatment. The results of water absorptivity of the resultant super water-absorbent polymer without surface crosslinking treatment are shown in Examples 5 to 7 in Table 3.

(II)-2 Surface Crosslinking Treatment;

Examples 8 to 10

10.0 g of the powder having the particle size of at least 63 μm obtained in (II)-1 was charged into a 200 mL improved coffee mill vessel and sprayed for several seconds with an aqueous solution of the following surface crosslinking agent by an air brush (OLYMPOS HP-83C). Then the powder was thermally treated and dried at 155° C. for 30 minutes to give surface crosslink-treated particles.

Aqueous solution of surface crosslinking agent: aqueous solution of 0.25 g of propylene glycol and 0.01 g of ethylene glycol diglycidyl ether in 0.25 g of deionized water.

The improved coffee mill was prepared by making two holes having a diameter of 1 cm on a top of a commercially available coffee mill, fixing with an adhesive tape, to one hole, a net having 325 mesh as a gas flow exit filter, and using the other hole as an introducing port for an air brush.

The results of the resultant super water-absorbent polymer with surface crosslinking treatment are shown in Examples 8 to 10 in Table 3.

Comparative Examples 4 to 17

The polymerization and the optional surface crosslinking treatment were conducted to give polymers with or without surface crosslinking treatment in the same manner as in Examples 5 to 10, except that the crosslinking agent (A) was replaced with crosslinking agent (a), (b) and (c) in the concentration shown in Table 3. The water absorptivity is shown in Comparative Examples 4 to 17 in Table 3.

Examples 11 to 16

(II)-3 Polymerization Reaction (Post-neutralization Polymerization Method)

180 g (2.5 mol) of acrylic acid and 100 mL of water were charged into a 1 L separable flask equipped with a nitrogen introducing tube, a thermometer, a dropping funnel and a stirrer, and stirred and cooled with ice under nitrogen atmosphere to have a temperature of about 10° C. A solution of 75 g (1.875 mol) of NaOH in water was dropwise added. The speed of dropwise adding the NaOH solution was adjusted so that the mixture temperature did not exceed 20° C. After the completion of addition of the NaOH solution, water was added so that the total amount of water was 424 g to give an aqueous solution having a monomer concentration of 32.4% and a neutralization ratio of 75% by mol. A crosslinking agent in the amount shown in Table 4 was added. The mixture was further cooled to about 5° C. while blowing nitrogen for at least 30 minutes.

After the reaction vessel was placed into a vessel filled with a thermally insulating material, a solution of 200 mg (0.74 mmol) of 2,2'-azobis(2-amidinopropane) dihydrochloride in 1 mL of water, a solution of 33.4 mg (0.19 mmol) of L-ascorbic acid in 1 mL of water, and a solution of 108 mg (0.98 mmol) of 31% aqueous hydrogen peroxide in 1 mL water were successively added within 30 seconds. The mixture increasingly had higher viscosity with evolving heat, and the stirring is discontinued after about 0.5 to 10 minutes. The reaction temperature reached a maximum temperature of 65° C. to 75° C. after about 10 to 20 minutes. The resultant gel was allowed to stand so as to be gradually cooled and was kept to stand for one night.

100 g of the resultant gel was placed into a rotary cutter, and comminuted to have particle size of about 1 mm.

The resultant comminuted gel was dried at 140° C. for 6 hours in an air flow oven with confirming a constant weight to give a dry solid. The resultant dry solid was treated with a sample mill, and sieved. The particles having a particle size of at least about 63 μm were taken as a super water-absorbent polymer without surface crosslinking treatment. The results of water absorptivity of the resultant super water-absorbent polymer without surface crosslinking treatment are shown in Examples 11 to 13 in Table 3.

(II)-4 Surface Crosslinking Treatment 10.0 g of the powder having the particle size of at least 63 μm obtained in (II)-3 was charged into a 200 mL improved coffee mill vessel and sprayed for several seconds with an aqueous solution of the following surface crosslinking agent by an air brush (OLYMPOS HP-83C). Then the powder was thermally treated and dried at 180° C. for 30 minutes to give surface crosslinking treatment particles.

Aqueous solution of surface crosslinking agent: aqueous solution of 0.33 g of ethylene carbonate in 0.150 g of deionized water.

The results of the super water-absorbent polymer with resultant surface crosslinking treatment are shown in Examples 11 to 16 in Table 4.

Comparative Examples 18 to 29

The polymerization and the optional surface crosslinking treatment were conducted to give polymers with or without surface crosslinking treatment in the same manner as in Examples 11 to 16, except that the crosslinking agent (A) was replaced with crosslinking agent (a), (b) and (c) in the concentration shown in Table 4. The results of water absorptivity are shown in Comparative Examples 18 to 29 in Table 4.

The water absorptivity under pressurized conditions is a scale of still exhibiting absorption property against a body weight when the polymer is used for, for example, a diaper. The water absorption property under pressurized conditions has a trade-off relationship with the CRC property which is a scale of water absorptivity under atmospheric pressure. The super water-absorbent polymer having high level of both properties has the preferable water absorptivity.

In the comparison of water absorptivity in the pre-neutralization polymerization method, when the water absorptivity of the super water-absorbent polymer after the surface treatment shown in Table 3 is focused, the super water-absorbent polymer prepared by using the crosslinking agent (A) according to the present invention (Examples 8, 9 and 10) exhibits better properties particularly under both of normal and pressurized conditions at the crosslinking agent concentration of 0.4% and better properties under pressurized conditions at the crosslinking agent concentration of 0.2% so as to be the super water-absorbent polymer having good balance of properties, in comparison with the polymer prepared according to Comparative Examples.

In comparison of the crosslinking agent of the present invention with the pentaerythritol triallyl ether (crosslinking agent (a)) which has been practically used as the allyl-based crosslinking agent and is recognized to have high properties, the crosslinking agent (a) has relatively poor water absorptivity particularly under pressurized conditions and can have similar property under pressurized conditions but has deteriorated water absorptivity under atmospheric pressure by increasing the crosslinking agent concentration to 1.0%. Additionally, the crosslinking agent (a) disadvantageously needs a large amount of used crosslinking agent.

Ethyleneglycol diallyl ether (crosslinking agent (b)) has further poor water absorptivity under pressurized conditions than the crosslinking agent (a).

The acryl-based trimethylolpropane triacrylate crosslinking agent (the crosslinking agent (c)) has significantly poorer water absorptivity than the crosslinking agent (a).

In the comparison of water absorptivity in the post-neutralization polymerization method, when the water absorptivity after the surface treatment shown in Table 4 is focused, the super water-absorbent polymer prepared by using the crosslinking agent (A) according to the present invention (Examples 14, 15 and 16) exhibits relatively poorer properties particularly under pressurized conditions in comparison with the polymer prepared by the pre-neutralization polymerization method, but exhibits better properties in comparison with the crosslinking agents (a), (b) and (c). That is, the present invention has better water absorptivity in comparison within the same preparation method.

TABLE 3

Pre-neutralization polymerization method: Water absorptivity of SAP

| crosslinking agent | crosslinking agent concentration (%) | SAP without surface crosslinking treatment | | | | SAP with surface crosslinking treatment | | | |
|---|---|---|---|---|---|---|---|---|---|
| | | | AC (g/g) after 1 hr | CRC (g/g) after 1 hr | | | AC (g/g) after 1 hr | CRC (g/g) after 1 hr | 0.7AUP (g/g) after 1 hr | 0.7AUP (g/g) after 24 hr |
| (A) | 0.20 | Ex. 5 | 48.0 | 44.3 | Ex. 8 | 41.9 | 38.1 | 24.1 | 29.0 |
| | 0.40 | Ex. 6 | 42.1 | 39.0 | Ex. 9 | 39.4 | 35.6 | 26.7 | 28.1 |
| | 0.80 | Ex. 7 | 41.4 | 37.7 | Ex. 10 | 38.6 | 33.8 | 25.9 | 30.9 |
| (a) | 0.40 | Com. Ex. 4 | 38.1 | 35.3 | Com. Ex. 11 | 38.0 | 35.1 | 15.5 | 24.7 |
| | 0.80 | Com. Ex. 5 | 39.2 | 36.2 | Com. Ex. 12 | 37.9 | 35.1 | 19.9 | 30.3 |
| | 1.00 | Com. Ex. 6 | 36.2 | 33.6 | Com. Ex. 13 | 33.7 | 31.3 | 25.2 | 27.9 |
| (b) | 0.40 | Com. Ex. 7 | 47.3 | 43.5 | Com. Ex. 14 | 41.3 | 37.7 | 13.1 | — |
| (c) | 0.20 | Com. Ex. 8 | 47.5 | 43.6 | Com. Ex. 15 | 41.2 | 38.0 | 16.3 | 25.1 |
| | 0.40 | Com. Ex. 9 | 40.8 | 37.8 | Com. Ex. 16 | 39.8 | 36.7 | 13.0 | 24.0 |
| | 0.80 | Com. Ex. 10 | 37.3 | 34.7 | Com. Ex. 17 | 35.6 | 33.1 | 14.6 | 25.8 |

SAP: Super water-absorbent polymer
Crosslinking agent concentration: % by weight based on charged acrylic acid at the polymerization reaction
Crosslinking agent (A): S-30 (Product in Example 4)
Crosslinking agent (a): P-30: Pentaerythritoltriallyl ether [Daiso Co. Ltd.]
Crosslinking agent (b): Ethyleneglycoldiallyl ether
Crosslinking agent (c): Trimethylolpropane triacrylate
AC: Absorbency Capacity
Water absorbance amount under atmospheric pressure
CRC: Centrifuge Retention Capacity
Water retention amount of water-absorbed polymer after centrifugal separation treatment
0.7AUP: Absorbency under Pressure
Water absorption amount under pressurized condition (0.7 psi)

TABLE 4

Post-neutralization polymerization method: Water absorptivity of SAP

| crosslinking agent | crosslinking agent concentration (%) | Non-post-crosslinked SAP | | | | Post-crosslinked SAP | | | |
|---|---|---|---|---|---|---|---|---|---|
| | | | AC (g/g) after 1 hr | CRC (g/g) after 1 hr | | | AC (g/g) after 1 hr | CRC (g/g) after 1 hr | 0.7AUP (g/g) after 1 hr | 0.7AUP (g/g) after 24 hr |
| (A) | 0.20 | Ex. 11 | 51.0 | 46.5 | Ex. 14 | 48.1 | 44.2 | 11.6 | 26.8 |
| | 0.40 | Ex. 12 | 41.8 | 38.3 | Ex. 15 | 40.3 | 36.9 | 15.7 | 26.7 |
| | 0.80 | Ex. 13 | 38.1 | 35.3 | Ex. 16 | 37.1 | 33.4 | 20.8 | 27.2 |
| (a) | 0.40 | Com. Ex. 18 | 30.9 | 29.4 | Com. Ex. 24 | 43.8 | 40.3 | 11.1 | 24.0 |
| | 0.80 | Com. Ex. 19 | 38.6 | 36.2 | Com. Ex. 25 | 41.0 | 37.9 | 10.7 | 24.7 |
| | 1.00 | Com. Ex. 20 | 24.8 | 23.1 | Com. Ex. 26 | 41.4 | 38.2 | 9.5 | 26.2 |
| (b) | 0.40 | Com. Ex. 21 | — | — | Com. Ex. 27 | 41.0 | 38.1 | 11.9 | — |
| (c) | 0.20 | Com. Ex. 22 | 42.8 | 39.8 | Com. Ex. 28 | 41.9 | 38.4 | 10.7 | 26.5 |
| | 0.40 | Com. Ex. 23 | 24.2 | 23.3 | Com. Ex. 29 | 28.1 | 26.5 | 12.5 | 22.9 |

SAP: Super water-absorbent polymer
Crosslinking agent concentration: % by weight based on charged acrylic acid at the polymerization reaction
Crosslinking agent (A): S-30 (Product in Example 4)
Crosslinking agent (a): P-30: Pentaerythritoltriallyl ether [Daiso Co. Ltd.]
Crosslinking agent (b): Ethyleneglycoldiallyl ether
Crosslinking agent (c): Trimethylolpropane triacrylate
AC: Absorbency Capacity
Water absorbance amount under atmospheric pressure
CRC: Centrifuge Retention Capacity
Water retention amount of water-absorbed polymer after centrifugal separation treatment
0.7AUP: Absorbency under Pressure
Water absorption amount under pressurized condition (0.7 psi)

EFFECT OF THE INVENTION

The crosslinking agent of the present invention can be used for the production of a super water-absorbent polymer comprising a polymerizable compound having a polymerizable double bond or a salt thereof. The crosslinking agent of the present invention is satisfactory in the solubility in an aqueous acrylate salt solution and can give an excellent super water-absorbent polymer which cannot be obtained in the prior arts, in view that high levels of both of water absorptivity under atmospheric pressure and water absorptivity under pressurized conditions are obtained and that the properties are obtained at the low concentration of the crosslinking agent. The crosslinking agent of the present invention can be practically used not only in the pre-neutralization polymerization method but also in the post-neutralization polymerization method.

The invention claimed is:

1. A super water-absorbent polymer prepared by polymerizing a polymerizable compound having a carbon-carbon double bond or a salt thereof in the presence of a crosslinking agent comprising a linear hydroxypolyallyl ether having at least one hydroxyl group and at least two allyl groups obtained by allyletherification of a hydroxyl group in a linear polyol compound which has a straight-chain carbon skeleton, and which has carbon atoms each having one hydroxyl group, and which is represented by the formula (1):

$$HOCH_2[CH(OH)]_nCH_2OH \quad (1)$$

wherein n is an integer of from 2 to 8.

2. The super water-absorbent polymer according to claim 1 which is crosslinked in an aqueous medium.

3. The super water-absorbent polymer according to claim 1, wherein the polymerizable compound also has a carboxyl group.

4. A super water-absorbent polymer prepared by polymerizing a polymerizable compound having a carbon-carbon double bond or a salt thereof in the presence of a crosslinking agent comprising a linear hydroxypolyallyl ether having at least one hydroxyl group and at least two allyl groups obtained by allyletherification of a hydroxyl group in a linear polyol compound which has a straight-chain carbon skeleton, and which has carbon atoms each having one hydroxyl group, and which is represented by the formula (1):

$$HOCH_2[CH(OH)]_nCH_2OH \quad (1)$$

wherein n is an integer of from 2 to 8, in which the super water-absorbent polymer is crosslinked in an aqueous medium and dried, and then surface crosslinking treated.

5. A method for the preparation of a super water-absorbent polymer which comprises polymerizing a polymerizable compound having a carbon-carbon double bond or a salt thereof in the presence of a linear hydroxypolyallyl ether having at least one hydroxyl group and at least two allyl groups obtained by allyletherification of a hydroxyl group in a linear polyol compound which has a straight-chain carbon skeleton, and which has carbon atoms each having one hydroxyl group, and which is represented by the formula (1):

$$HOCH_2[CH(OH)]_nCH_2OH \quad (1)$$

wherein n is an integer of from 2 to 8.

6. A method for the preparation of a super water-absorbent polymer which comprises polymerizing a polymerizable compound having a carbon-carbon double bond or a salt thereof in the presence of a linear hydroxypolyallyl ether having at least one hydroxyl group and at least two allyl groups obtained by allyletherification of a hydroxyl group in a linear polyol compound which has a straight-chain carbon skeleton, and which has carbon atoms each having one hydroxyl group, and which is represented by the formula (1):

$$HOCH_2[CH(OH)]_nCH_2OH \qquad (1)$$

wherein n is an integer of from 2 to 8, in which the super water-absorbent polymer is crosslinked in an aqueous medium and dried, and then surface crosslinking treated.

7. The super water-absorbent polymer according to claim 4, wherein the polymerizable compound also has a carboxyl group.

* * * * *